(12) United States Patent
McDaniel

(10) Patent No.: US 7,217,259 B2
(45) Date of Patent: May 15, 2007

(54) INTERLABIAL ABSORBENT ARTICLE

(75) Inventor: Mary L. McDaniel, Appleton, WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 320 days.

(21) Appl. No.: 10/323,864

(22) Filed: Dec. 18, 2002

(65) Prior Publication Data

US 2004/0122402 A1 Jun. 24, 2004

(51) Int. Cl.
*A61F 13/26* (2006.01)
*A61F 13/51* (2006.01)
*A61F 13/34* (2006.01)
*A61F 13/28* (2006.01)

(52) U.S. Cl. .............. 604/385.17; 604/360; 604/363; 604/364; 604/385.01; 604/387

(58) Field of Classification Search .......... 604/385.01, 604/385.17–385.18, 387; 15/143.1, 145
See application file for complete search history.

(56) References Cited

U.S. PATENT DOCUMENTS

| | | | | |
|---|---|---|---|---|
| 2,682,875 A | * | 7/1954 | Brown | .................. 604/374 |
| 3,420,235 A | | 1/1969 | Harmon | |
| 3,726,277 A | | 4/1973 | Hirschman | |
| 3,905,372 A | * | 9/1975 | Denkinger | .................. 604/359 |
| 3,983,873 A | | 10/1976 | Hirschman | |
| 4,175,561 A | | 11/1979 | Hirschman | |
| 4,341,217 A | | 7/1982 | Ferguson et al. | |
| 4,481,243 A | * | 11/1984 | Allen | ................... 428/154 |
| 4,595,392 A | * | 6/1986 | Johnson et al. | ........ 604/385.17 |
| 4,938,515 A | * | 7/1990 | Fazio | ................... 294/25 |
| 5,460,624 A | | 10/1995 | Ahr et al. | |
| 5,484,429 A | | 1/1996 | Vukos et al. | |
| 5,525,345 A | * | 6/1996 | Warner et al. | ............. 424/402 |

(Continued)

FOREIGN PATENT DOCUMENTS

EP 0161663 11/1985

(Continued)

OTHER PUBLICATIONS

U.S. Appl. No. 10/732,163, filed Dec. 10, 2003.

(Continued)

*Primary Examiner*—Karin Reichle
(74) *Attorney, Agent, or Firm*—Dority & Manning, P.A.

(57) ABSTRACT

An interlabial absorbent article is provided for disposition primarily within the vestibule of a female wearer. The article includes a liquid permeable top sheet, a polymeric film back sheet, and an absorbent material disposed between the top sheet and back sheet. The polymeric film back sheet is also liquid permeable such that the article may be disposed at generally any orientation within the wearer's vestibule and absorb bodily fluids at any such orientation.

15 Claims, 4 Drawing Sheets

U.S. PATENT DOCUMENTS

| | | |
|---|---|---|
| 5,573,523 A | 11/1996 | Whalen et al. |
| 5,605,764 A | 2/1997 | Miller et al. |
| H1670 H * | 7/1997 | Aziz et al. ................. 604/367 |
| 5,693,707 A | 12/1997 | Cheng et al. |
| 5,738,212 A * | 4/1998 | Pollard et al. .............. 206/362 |
| 5,762,644 A * | 6/1998 | Osborn et al. ......... 604/385.17 |
| 5,827,256 A * | 10/1998 | Balzar .................. 604/385.18 |
| 5,944,705 A * | 8/1999 | Ducker et al. .............. 604/364 |
| 6,063,858 A | 5/2000 | Daniels et al. |
| 6,132,841 A * | 10/2000 | Guthrie et al. .............. 428/132 |
| 6,319,238 B1* | 11/2001 | Sartorio et al. ............. 604/330 |
| 6,514,602 B1 | 2/2003 | Zhao et al. |
| 2001/0000796 A1 | 5/2001 | Osborn et al. |
| 2001/0001815 A1 | 5/2001 | Osborn et al. |
| 2001/0025163 A1 | 9/2001 | Brown et al. |
| 2002/0058921 A1 | 5/2002 | Sigl |
| 2003/0225388 A1 | 12/2003 | Bhavani |
| 2004/0018366 A1 | 1/2004 | George et al. |
| 2004/0019168 A1 | 1/2004 | Soerens et al. |
| 2004/0043688 A1 | 3/2004 | Soerens et al. |

FOREIGN PATENT DOCUMENTS

| | | |
|---|---|---|
| EP | 888762 A1 * | 1/1999 |
| WO | 9808475 | 3/1998 |
| WO | WO 00/69481 A1 * | 11/2000 |
| WO | 2004 011046 A1 | 2/2004 |
| WO | 2004 060248 A1 | 7/2004 |

OTHER PUBLICATIONS

U.S. Appl. No. 10/732,827, filed Dec. 10, 2003.

PCT Search Report, Dec. 29, 2003.

* cited by examiner

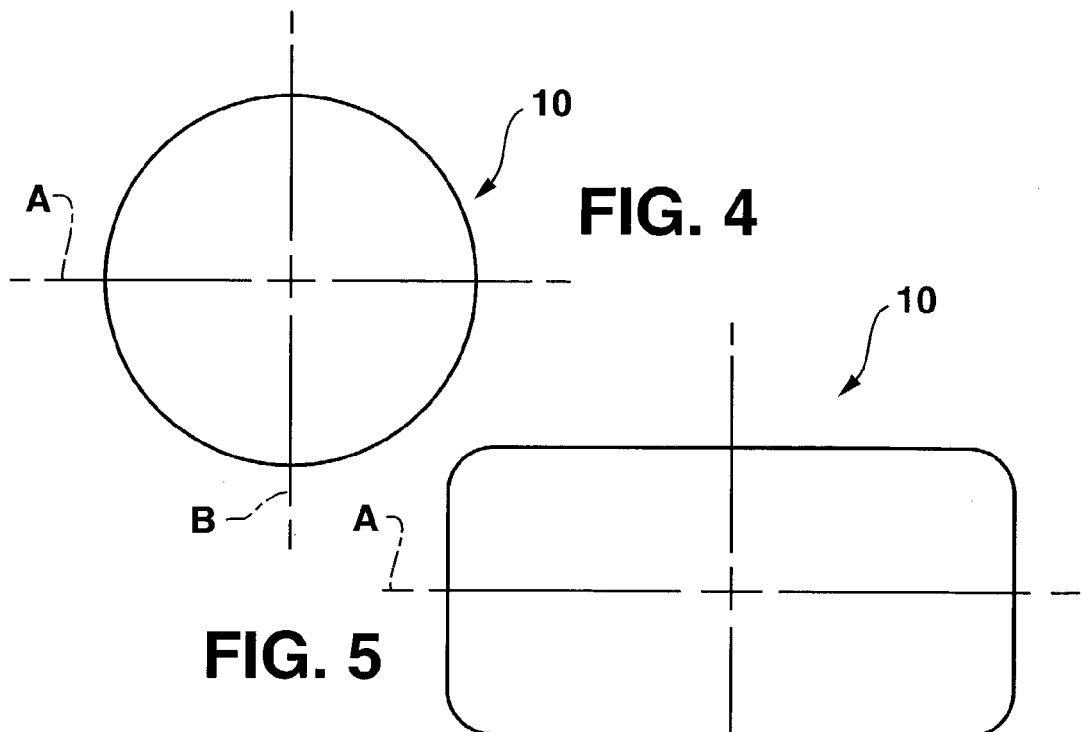
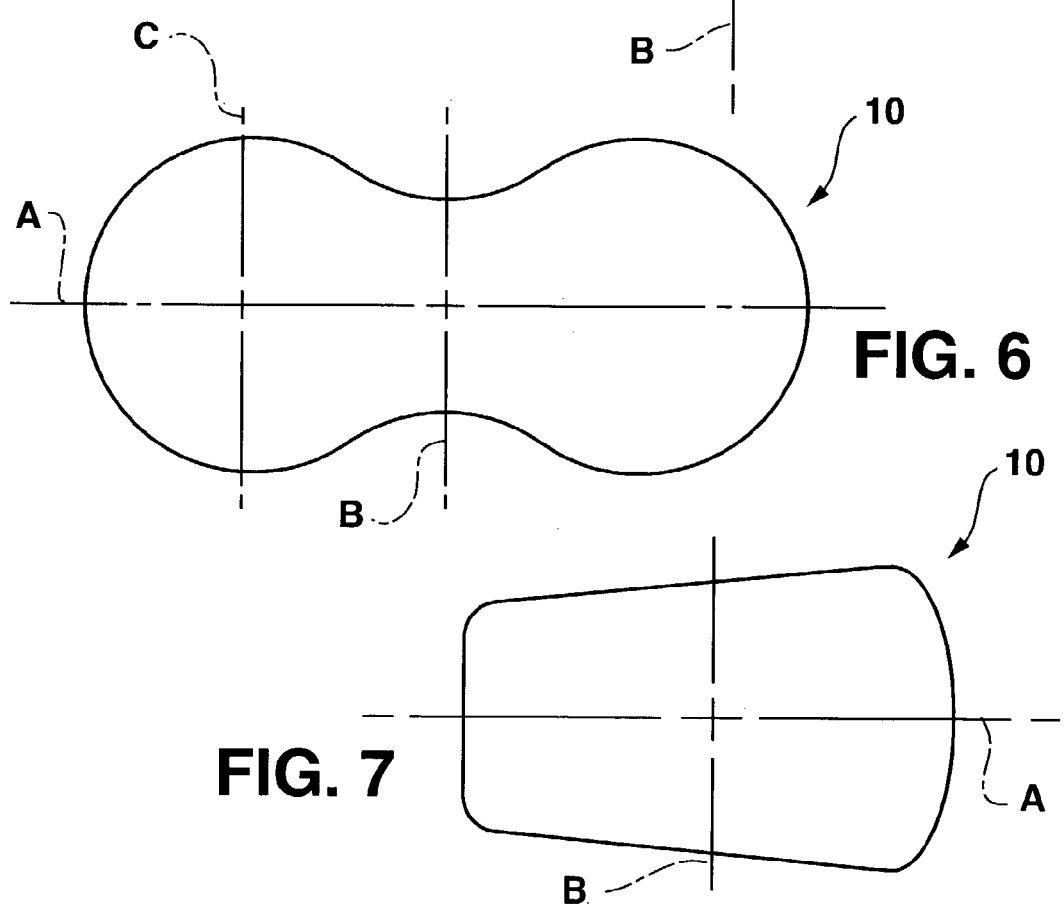
FIG. 4
FIG. 5
FIG. 6
FIG. 7

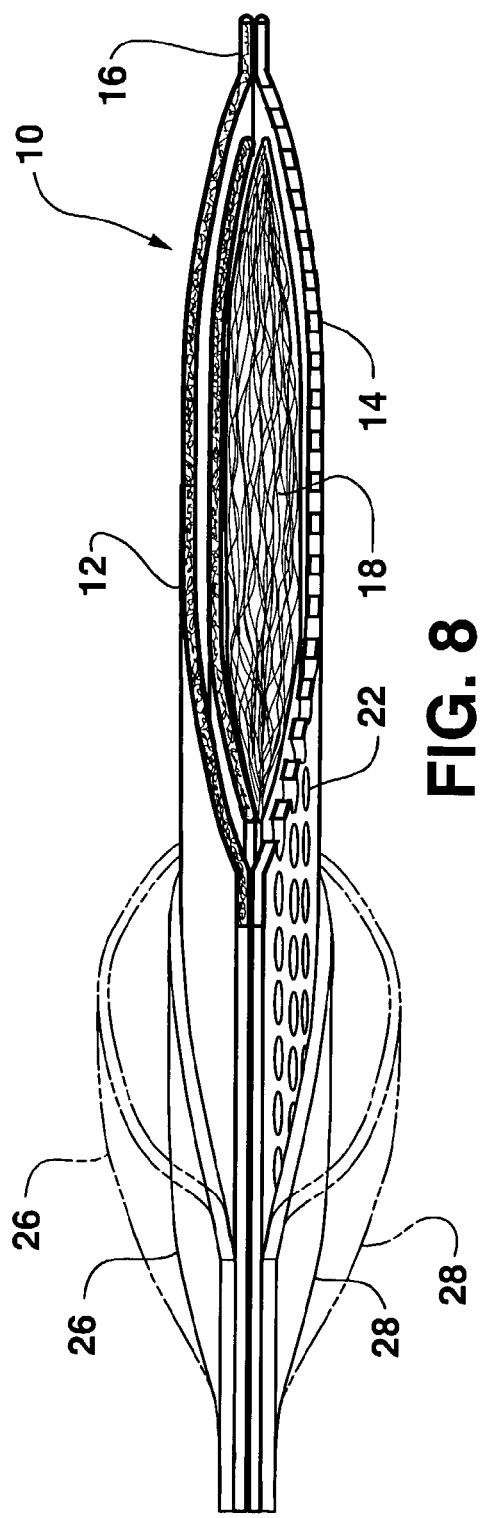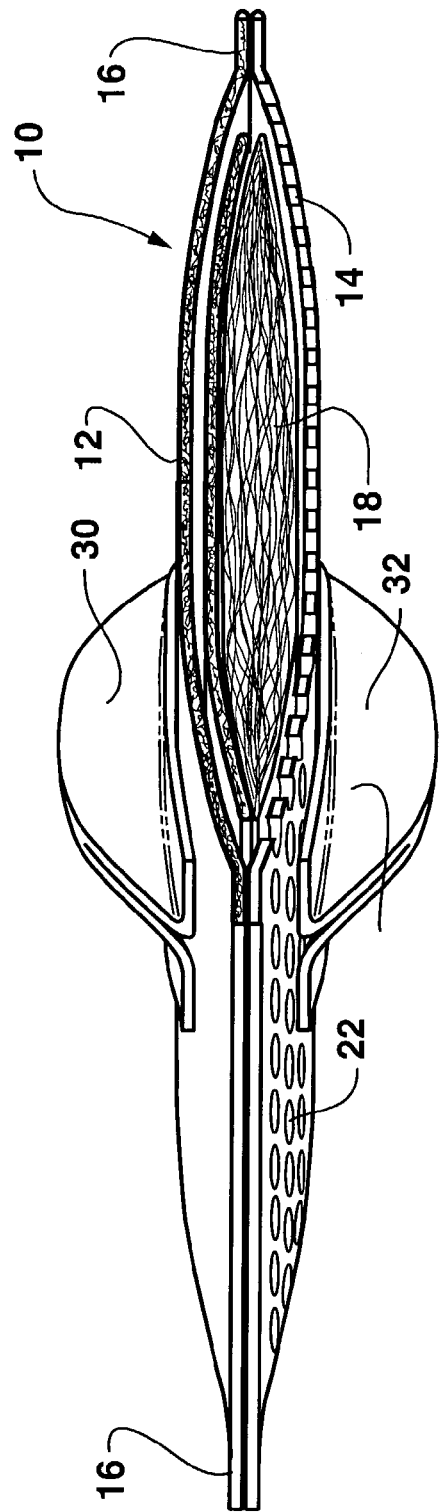

INTERLABIAL ABSORBENT ARTICLE

FIELD OF THE INVENTION

The present invention relates to the field of feminine hygiene products, and more particularly to interlabial absorbent articles.

BACKGROUND

A broad range and wide variety of absorbent articles configured for absorption of bodily exudates such as menstrual fluid are well known. With respect to feminine hygiene, the art has offered two basic types of feminine hygiene protection: namely sanitary napkins and panty liners, developed for external wear about the pudendum region, and tampons, developed for placement within the vaginal cavity, and accordingly for interruption of menstrual flow therefrom prior to such menstrual flow reaching the vestibule. Hybrid feminine hygiene protection devices, attempting to merge the structural features of both sanitary napkins and tampons in a single type of device, have also been proposed, but have not seen a meaningful measure of acceptance insofar as the effort to achieve advantages with such devices has been overshadowed by the more demonstrable perception of structural and anatomically functional disadvantages.

Other less intrusive devices, known as labial or interlabial devices or pads, have also been proposed. These articles are designed to reside primarily within the wearer's vestibule while having a portion residing at least partially external of the wearer's vestibule. Interlabial articles can provide a preferred profile or appearance when viewed through a wearer's outer garments and do not have the same problems of reliance on swelling within the vaginal canal as required by tampons. U.S. Pat. Nos. 5,484,429; 4,175,561; 3,983,873; and 3,726,277 disclose various types of interlabial absorbent articles.

A significant factor affecting consumer acceptance of interlabial articles is comfort and ease of use. However, there is great variance in the elasticity and dimensions of the labial/vestibule region between women. Vestibule lengths may range from 15–100 mm, and widths may range from 5–50 mm. Such variance is problematic for manufacturers in that it is difficult to provide an interlabial article that is comfortable for a wide range of women.

The design of conventional interlabial articles is also restrictive in terms of product versatility. For instance, the majority of interlabial articles have a pervious top sheet and an impervious back sheet. This design restricts article orientation and placement in that the pervious top sheet must always be the body-facing side of the article. This inhibits repositioning of the article to relieve discomfort. For example, depending on a wearer's unique anatomical configuration and the interlabial product size and shape, the interlabial article may cause rubbing/chaffing in the wearer's perineum region. Options for repositioning the article to relieve such rubbing/chaffing are severely restricted by the presence of the impervious back sheet. Also, the chance of article misplacement (impervious side to the vaginal opening) is always a possibility.

Thus, a need exists for an interlabial article design that offers a greater degree of comfort and versatility to a wider range of women. The present invention provides such a design.

SUMMARY

Objects and advantages of the invention will be set forth in part in the following description, or may be obvious from the description, or may be learned through practice of the invention.

The present invention relates to a unique configuration for a feminine care interlabial absorbent article that offers distinct advantages to wearers over conventional devices. The interlabial absorbent article includes a liquid permeable top sheet, a polymeric film back sheet, and an absorbent material disposed between the top sheet and back sheet. The polymeric film back sheet is rendered liquid permeable such that the article may be disposed at generally any orientation within the wearer's vestibule and absorb bodily fluids at any such orientation. The present invention recognizes that conventional interlabial absorbent article designs incorporating a liquid repellent or liquid impervious film back sheet limit the versatility of such products and may add to the discomfort felt by certain users. On the other hand, there are characteristics of a polymeric film back sheet that are desirable. For example, some women find the feel of the polymeric film to be soothing as compared to the typical nonwoven top sheet, particularly against dry or irritated skin. With the configuration according to the present invention, either side of the article (back sheet or top sheet) may serve as the body facing surface of the article.

Also, with the present design wherein either side of the article is liquid permeable, the absorbent article may be folded into virtually any configuration to adapt the device to a wearer's particular anatomical make-up. Thus, a particular size or shape of interlabial article may be used by a wider range of women.

In one particular embodiment, either or both of the top sheet and film back sheet may be embossed. The embossing improves fluid intake through the covers to the absorbent material.

In another desirable embodiment, either or both of the top sheet and film back sheet may contain a skin wellness additive. This additive may be, for example, a lotion formulation designed particularly to address a skin or other health issue particular to the female vestibule. The lotion formulation may be any one or combination or emollients, waxes, and skin protectant agents known to those skilled in the art.

In another embodiment, the interlabial absorbent article may include placement mechanisms attached to the top sheet and back sheet. The placement mechanisms may be, for example, a retainer flap or a tab, and are intended to aid the wearer in placement and removal of the article. The mechanisms are removable from their respective sheets so that, prior to placement, the wearer may remove the mechanism from the side of the article intended to be the body-facing side. The remaining mechanism may be used to place the article and to remove the article.

Aspects of the invention will be described in greater detail below by reference to embodiments illustrated in the attached drawings.

BRIEF DESCRIPTION OF THE DRAWINGS

FIG. 4 is a diagrammatic view of an interlabial absorbent article configuration in accordance with the invention.

FIG. 5 is a diagrammatic view of an interlabial absorbent article configuration in accordance with the invention.

FIG. 6 is a diagrammatic view of an interlabial absorbent article configuration in accordance with the invention.

FIG. 7 is a diagrammatic view of an interlabial absorbent article configuration in accordance with the invention.

FIG. 8 is a cross-sectional view of an embodiment of an interlabial absorbent article according to the invention with retainer flaps.

FIG. 9 is a cross-sectional view of an embodiment of an interlabial absorbent article according to the invention with placement tabs.

DETAILED DESCRIPTION

Figure 1:
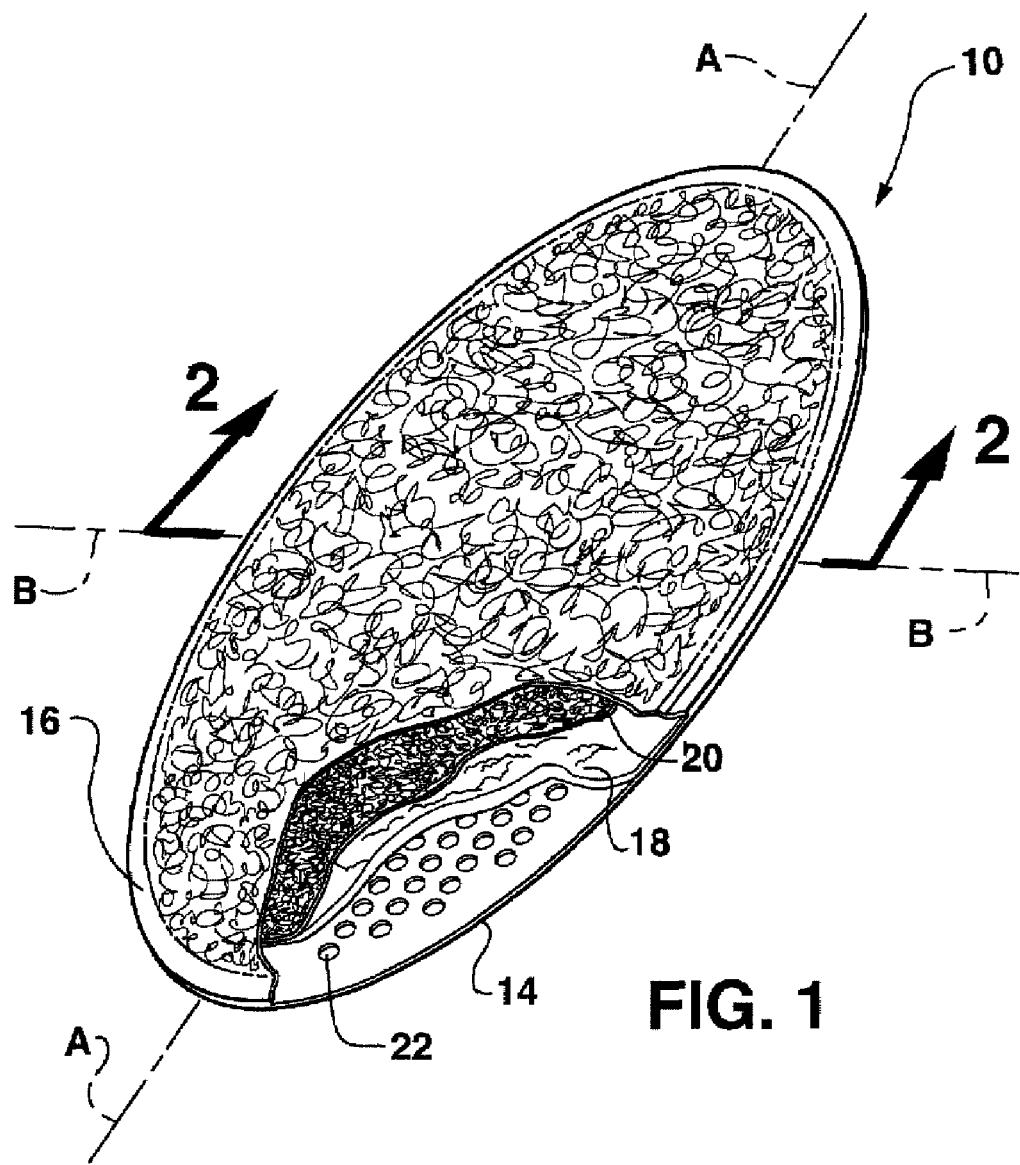
FIG. 1 is a perspective and partial cut-away view of an interlabial absorbent article in accordance with the invention.

Reference will now be made in detail to embodiments of the invention, one or more examples of which are illustrated in the drawings. Each embodiment and example are provided for purposes of explaining the invention, and are not meant as a limitation of the invention. For example, features illustrated or described as part of one embodiment may be used with another embodiment to yield still a further embodiment. It is intended that the present invention include these and other modifications and variations as come within the scope and spirit of the invention.

As used herein, the term "interlabial absorbent article" refers to a device having at least one absorbent component, and which is specifically configured for disposition between the labia majora, extending at least partially into the vestibule of a female wearer during use. The vestibule is considered to the be the region defined within the labia beginning at about a point lying caudally from the anterior labial commissure and extending rearward to the posterior labial commissure, and bounded inwardly by the floor of the vestibule. One of skill in the art fully understands that there is a wide range of variation among women with respect to the relative size and shape of labia majora and labia minora as the same interrelatedly define the contour of the vestibule. For purposes of the present description, however, such differences will not specifically be addressed, it being recognized that in any event the disposition of the absorbent article into the vestibule necessitates placement between the labia majora regardless of any such consideration respecting the labia minora. An interlabial absorbent article is disposed at least partially within the vestibule for at least partially occluding the vestibule with respect to fluid flow from the vestibule. In this regard, the predominant use of the absorbent article is for the absorption of menstrual fluid emitted via the vaginal orifice, although the article is equally well adapted to serve as a type of incontinence device for absorption of urine as occurs upon minor, female incontinence.

The present invention provides an interlabial absorbent article configured for disposition primarily within the vestibule of a female wearer. As described in greater detail below, the article may take on any suitable overall shape and configuration. The article includes a liquid permeable top sheet, a polymeric film back sheet, and an absorbent material disposed between the top sheet and back sheet. The polymeric film back sheet is made liquid permeable, for example by aperturing, such that the article may be disposed at generally any orientation within the wearer's vestibule and absorb bodily fluids at any such orientation. This is accomplished without eliminating the polymeric back sheet that may be desired to particular consumers.

The fact that the article may absorb bodily fluids from either surface results in numerous benefits. For example, the article may be placed in any direction, or folded into any desired configuration, by the wearer to conform to their unique anatomical characteristics and provide maximum comfort to the wearer. The design allows the wearer to position the article for maximum article contact with the labia minora sides/edges and vestibule floor depending on the coverage the wearer desires.

Because both faces of the article are permeable to bodily fluids, a wearer may stack the articles for additional absorbency and odor protection. Multiple articles may be folded into each other, and so forth.

The possibility of article misplacement is eliminated with the interlabial article design according to the invention.

It should be appreciated that virtually any configuration of a single article or multiple articles are possible with the interlabial device of this invention. For example, the article may be C-folded, e-folded, bi-folded, flat, etc. Multiple articles may be layered, stacked, side-by-side, etc. One article may be wrapped within another article, and so forth. Such options are available without an impervious back sheet blocking fluid transfer between articles.

Referring to the figures in general, various embodiments of an interlabial absorbent article 10 are illustrated. The absorbent article 10 includes a top sheet 12, a back sheet 14, and an absorbent material 18 sandwiched between the top sheet 12 and back sheet 14. The top sheet 12 and back sheet 14 are sealed together at their edges 16, the sealed edges 16 defining an overall geometry for the article 10. The article 10 should be of a suitable size and shape to allow at least a portion, preferably a major portion, of the absorbent article to be disposed within the vestibule of a female wearer. In addition, the absorbent article 10 desirably at least partially occludes and intercepts the flow of menstrual fluid, urine or other bodily exudates from the wearer's vaginal orifice and/or urethral orifice.

Figure 2:
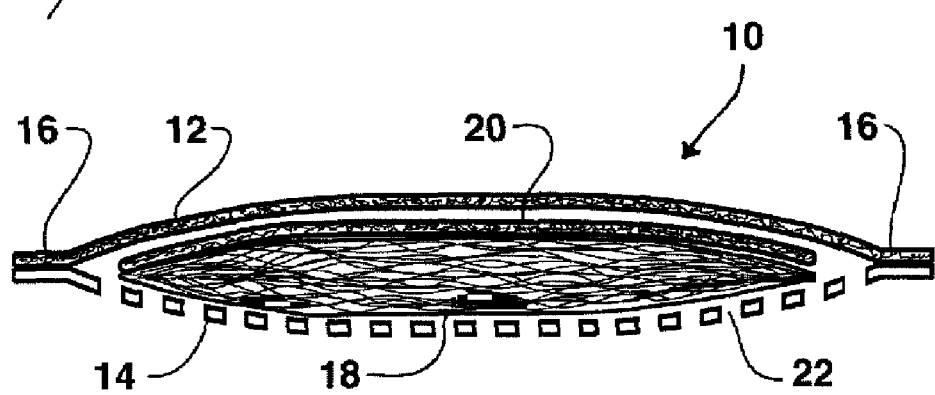
FIG. 2 is a cross-sectional view of the article of FIG. 1 taken along the lines indicated.

The article 10 is not limited to any particular shape or configuration. In the embodiments of FIGS. 1 and 2, for example, the article 10 has an overall oval shape and is thus symmetric with respect to a longitudinal axis A and a transverse axis B. It may be desired that the article have a shape symmetric to both the longitudinal and transverse axis so that the wearer need not be concerned with orientation of the device, particularly if the article 10 is to be folded, rolled, or otherwise shaped. Various other suitable symmetric shapes are illustrated in FIGS. 4, 5, and 6. FIG. 4 illustrates a generally circular article 10. FIG. 5 illustrates a generally rectangular article 10 with rounded corners. FIG. 6 illustrates a generally dog-bone shaped article 10. In certain applications, it may be desired that the article 10 have a non-symmetric shape and have, for example, increased absorbency at one end as compared to another. Such an embodiment is illustrated in FIG. 7 as a generally trapezoidal shaped article 10.

The geometry of the absorbent material 18 is a significant factor affecting the overall size, shape, and effectiveness of the absorbent article 10. In general, the absorbent 18 has a maximum width and a minimum width as measured in the transverse plane of axis B. In the embodiment of FIG. 5, the maximum and minimum widths are the same. In the embodiment of FIG. 6, the minimum width is defined at the axis B and the maximum width at the axis C. The maximum width of the absorbent 18 typically is no greater than about 30 mm;

alternatively, no greater than about 40 mm; alternatively, no greater than about 50 mm; alternatively, no greater than about 60 mm; or alternatively, no greater than about 70 mm. The minimum width of the absorbent 18 typically is no less than about 30 mm; alternatively, no less than about 20 mm; alternatively, no less than about 10 mm; or alternatively, no less than about 5 mm. Thus, the absorbent material 18 can have a width ranging from no less than about 5 mm up to no greater than about 70 mm; although the approximate width(s) of the absorbent can vary according to, inter alia, the general design and intended disposition of the absorbent article 10 within the vestibule of a female wearer.

The absorbent material 18 also has a maximum length measured along the principal longitudinal axis A of the article. The maximum length of the absorbent material 18 typically is no greater than about 40 mm; alternatively, no greater than about 50 mm; alternatively, no greater than about 60 mm; alternatively, no greater than about 70 mm; alternatively, no greater than about 80 mm; alternatively, no greater than about 90 mm; or alternatively, no greater than about 100 mm.

The absorbent article 10 is desirably provided with sufficient capacity to absorb and retain the intended amount and type of bodily exudate(s). The absorbent capacity is provided by a fluid retentive core made up of the absorbent material 18. The absorbent material 18 can have an absorbent capacity ranging from no less than about 1 g/g up to no greater than about 30 g/g; although the approximate capacity of the absorbent can vary according to, inter alia, the general design and intended disposition of the absorbent article 10 within the vestibule of a female wearer. One of skill in the art will readily realize that the addition of superabsorbent polymer or coated superabsorbent polymer) to the absorbent material 18 typically has the effect of substantially increasing the absorbent capacity.

Further, the size and absorbent capacity of the absorbent material 18 can be varied with the dimension, shape, and configuration of the absorbent material. For example, the absorbent can have a varying thickness with in the article 10, or can have a hydrophilic gradient, or can contain superabsorbent polymer(s) and the like. The absorbent material 18 will generally have a thickness of about 10 mm or less; although the approximate thickness of the absorbent can vary according to, inter alia, the general design and intended disposition of the absorbent article 10 within the vestibule of a female wearer.

The absorbent material 18 can include any material capable of absorbing and/or adsorbing and thereafter retaining the intended bodily exudate(s). Suitable materials are also generally hydrophilic, compressible and conformable. The absorbent material 18 can be formed from any of the materials well known to those of ordinary skill in the art. Examples of such materials include, but are not limited to, various natural or synthetic fibers, multiple plies of creped cellulose wadding, fluffed cellulose fibers, rayon or other regenerated cellulose materials, wood pulp fibers or comminuted wood pulp fibers, airlaid material, textile fibers, a blend of polyester fibers and polypropylene fibers, absorbent foams, absorbent sponges, superabsorbent polymers, coated superabsorbent polymers, fibrous bundles or nits, or any equivalent material or combination of materials. Hydrophobic materials are also suitable for use where the hydrophobic material has been rendered hydrophilic according to any of a number of known methods for so doing.

The absorbent material 18 desirably also has a relatively low density which is desirable for comfort. Generally, the absorbent material 18 has a density that can range up to about 0.5 g/cc; although the approximate density of the absorbent can vary according to, inter alia, the general design and intended disposition of the absorbent article 10 within the vestibule of a female wearer.

The absorbent material 18 can have a basis weight of about 600 gsm or less; although the approximate basis weight of the absorbent can vary according to, inter alia, the general design and intended disposition of the absorbent article 10 within the vestibule of a female wearer.

A specific example of a suitable absorbent material 18 is a coform material made of a blend of polypropylene and cellulose fibers such as that used in KOTEX maxi pantiliners and obtainable from Kimberly-Clark Corporation, Neenah, Wis., USA.

The fluid permeable cover or top sheet 12 has an outwardly facing surface that may contact the body of the wearer and receive bodily exudate(s). The top sheet 12 desirably is made of a material which is flexible and non-irritating to the tissues within the vestibule of a female wearer. As used herein, the term "flexible" is intended to refer to materials which are compliant and readily conform to the bodily surface(s) with which such materials are in contact, or materials which respond by easily deforming in the presence of external forces.

The top sheet 12 is provided for comfort and conformability and functions to direct bodily exudate(s) away from the body, through the top sheet 12 and toward the absorbent material 18. The top sheet 12 should retain little or no liquid in its structure so that the cover provides a relatively comfortable and non-irritating surface next to the tissues within the vestibule of a female wearer. The top sheet 12 can be constructed of any woven or nonwoven material which is easily penetrated by bodily fluids which contact the surface of the cover. Examples of suitable cover materials include rayon, bonded carded webs of polyester, polypropylene, polyethylene, nylon, or other heat-bondable fibers, polyolefins, such as copolymers of polypropylene and polyethylene, linear low-density polyethylene, and aliphatic esters such as polylactic acid. Finely perforated film webs and net material can also be used. A specific example of a suitable cover material is a bonded carded web made of polypropylene and polyethylene such as that used as cover stock for KOTEX pantiliners and obtainable from Sandler Corporation, Germany. Other examples of suitable materials are composite materials of polymer and nonwoven fabric materials. The composite materials are typically in the form of integral sheets generally formed by the extrusion of a polymer onto a web of spunbonded material. The fluid permeable cover 12 can also contain a plurality of apertures (not shown) formed therein which are intended to increase the rate at which bodily fluid(s) can penetrate through the cover and into the absorbent material 18.

A physiologically hydrous top sheet material is also suitable for use. As used herein, the phrase "physiologically hydrous" is intended to connote a sheet material which maintains a suitably moist interface between the tissues of the vestibule and the absorbent article 10 when disposed in the vestibular environment; material which is benign respecting the requirements of comfort associated with the interposition of fabric or fabric-like structures within the moist tissue environment of the vestibule, also considering that the absorbent article receives bodily fluid(s) migrating through the vestibule and conducts such fluids to the absorbent material 18. Thus, while the top sheet 12 is not "hydrous" in the classic sense prior to use, inasmuch as the sheet is dry at that time, the top sheet 12 maintains, or at least does not interfere with the maintenance of, the proper moisture level or moisture balance required within the vestibule for proper maintenance of tissue health within the vestibule.

At least a portion of the surface of the top sheet 12 can be treated with a surfactant in order to render the cover more hydrophilic. This results in permitting the insulting bodily fluid(s) to more readily penetrate the material The surfactant can also diminish the likelihood that the insulting bodily fluid(s), such as menstrual fluid, will flow off the top sheet 12 rather than passing through the cover and being absorbed by the absorbent material 18. One suitable approach provides for the surfactant to be substantially evenly distributed across at least a portion of the upper surface of the top sheet 12 which overlies the upper surface of the absorbent material 18.

Figure 3A:
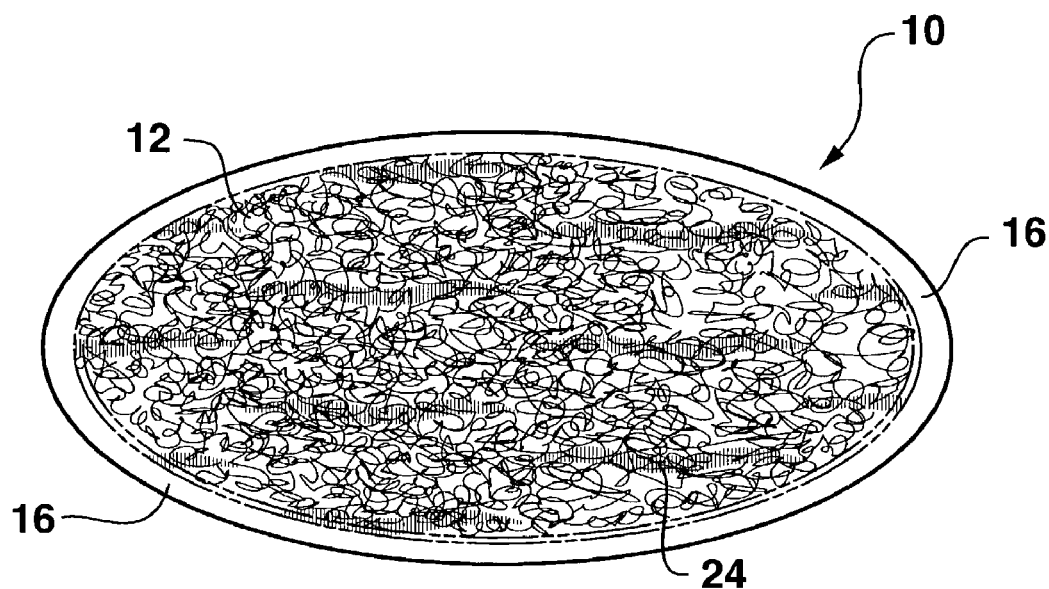
FIGS. 3A and 3B are planar views of a top sheet and back sheet of an embodiment of an interlabial absorbent article in accordance with the invention.

The top sheet 12 may also be embossed, as generally illustrated in FIG. 3*a*, with any desired embossing pattern to define embossed channels 24. Embossing techniques are well known to those skilled in the art. An embossing pattern not only creates an aesthetically pleasing surface, the channels 24 facilitate intake of menses fluid. Menses will tend to flow along the densified edges of the channels 24 rather than pool on contact points of the top sheet 12.

The top sheet 12 can be maintained in secured relation with the absorbent material 18 by bonding all or a portion of the adjacent surfaces to one another. A variety of bonding methods known to one of skill in the art can be utilized to achieve any such secured relationship. Examples of such methods include, but are not limited to, the application of adhesives in a variety of patterns between the two adjoining surfaces, entangling at least portions of the adjacent surface of the absorbent with portions of the adjacent surface of the cover, or fusing at least portions of the adjacent surface of the cover to portions of the adjacent surface of the absorbent.

It may also be desired to include a wicking layer or surge material 20 between the top sheet 12 and absorbent material 18, as generally illustrated in FIGS. 1 and 2. Surge materials are well known in the art and serve to rapidly intake bodily exudates through the top sheet 12 at a rate generally greater than the absorbent material could, and to distribute the exudates to the underlying absorbent material 18.

The top sheet 12 and back sheet 14 have periphery edges joined together to form a sealed circumferential edge 16 of the article 10 utilizing known techniques, such as, for example, gluing, crimping, hot-sealing or the like.

Figure 3B:
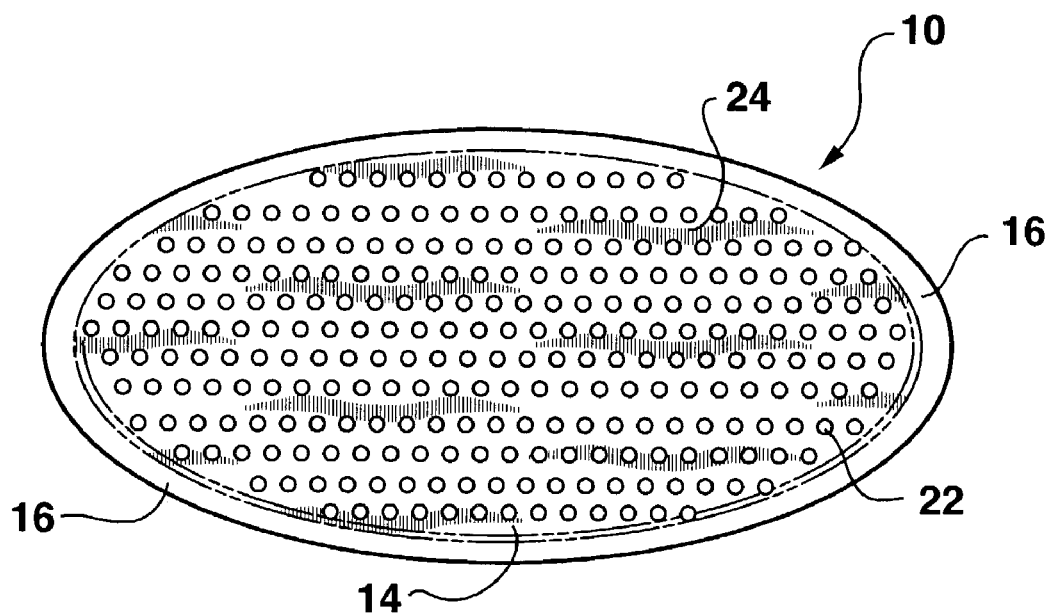

As discussed, there may be configurations of the article 10 (e.g., folded, rolled, stacked, etc.) wherein the back sheet 14 of the article 10 is oriented to receive bodily exudates. Certain consumers also prefer the feel of a polymeric film against their skin or other sensitive areas as compared to typical nonwoven cover sheet materials. Thus, a versatile article 10 according to the invention includes a polymeric film back sheet material that is also fluid pervious so as not to detract from the versatility of the article. The back sheet 14 may have the same or greater degree of fluid perviousness as the top sheet 12. The back sheet 14 is formed of a generally fluid impervious film that has been rendered fluid pervious by known mechanical or chemical techniques. For example, the film may be needled or calendared such that apertures 22 are defined therethrough in any desired pattern. In this way, menses or other bodily exudates are readily conducted through the back sheet 14 to the underlying absorbent material 18. As with the top sheet 12, the back sheet 14 may also be treated with a surfactant, or may also be embossed to define embossed channels 24, as illustrated in FIG. 3B. A surge layer may also be disposed between the back sheet 14 and absorbent material 18.

The back sheet 14 may also be a breathable film material to permit passage of air and moisture vapor out of the absorbent material 18. An example of a suitable film material for the back sheet 14 is a micro-embossed, polymeric film, such as polyethylene, polypropylene or polyester, having a minimum thickness of no less than about 0.025 mm and a maximum thickness of no greater than about 0.13 mm. Bicomponent films can also be used, as well as woven and nonwoven fabrics which have been treated to render such fabrics liquid-impermeable. An example of another suitable material is a closed cell polyolefin foam, for example, a closed cell polyethylene foam. Any such materials may be apertured or otherwise rendered fluid permeable.

Apertured films may be particularly desired for use as the polymeric back sheet 14 because they are permeable to bodily exudates, are non-absorbent, and have a reduced tendency to allow liquids to pass back through and rewet the wearer's skin. The apertures may be tapered to enhance this characteristic. Thus, the surface of the formed film in contact with the body remains dry, thereby reducing body soiling and creating a more comfortable feel for the wearer. Examples of suitable liquid pervious formed films are described in U.S. Pat. Nos. 3,929,135; 4,324,246; 4,342, 314; 4,463,045; and 5,006,394, such patents incorporated herein by reference for all purposes.

The back sheet 14 can be maintained in secured relation with the absorbent material 18 by bonding all or a portion of the adjacent surfaces to one another. A variety of bonding methods known to one of skill in the art can be utilized to achieve any such secured relation. Examples of such methods include, but are not limited to, ultrasonic bonding, thermal bonding, or the application of adhesive materials in a variety of patterns between the two adjoining surfaces. A specific example of a back sheet material is a polyethylene film such as that used in KOTEX pantiliners and obtainable from Pliant Corporation, Schaumburg, Ill., USA.

As mentioned, either or both, of the top sheet 12 and back sheet 14 may be treated with a skin wellness additive designed to address skin health issues particular to the use of interlabial devices. The additive may be applied uniformly onto the materials, or in discrete localized deposits on the outwardly facing surfaces of the sheets 12 and 14. These additives provide an increased skin wellness benefit in that they offer an enhanced degree of lubricity and protection to targeted areas within the female vestibule. The quantity of the additive may vary depending on the desired skin wellness benefit and may be, for example, within a range of about 0.5% to about 50% of the total weight of the sheet materials.

In one embodiment, the top sheet 12 and back sheet 14 may be treated with a surfactant that includes a skin wellness additive, or a skin wellness additive may be applied in an additional overall coating process.

In an alternate embodiment, the skin wellness additive may be in the form of discrete localized deposits of lotion formulation on the outwardly facing surfaces of the top sheet 12 and back sheet 14. The lotion formulation may include any one or combination of emollients, and may also include one or more waxes. A viscosity enhancer may also be included. The lotion formulation may include other ingredients as well.

An emollient acts as a lubricant to reduce the abrasiveness of the sheets to the skin and, upon transfer to the skin, helps to maintain the soft, smooth and pliable characteristics of the skin. Suitable emollients which can be incorporated into the lotion formulation include oils such as petroleum based oils, vegetable based oils, mineral oils, natural or synthetic oils, silicone oils, lanolin and lanolin derivatives, kaolin and kaolin derivatives and the like and mixtures thereof; esters such as cetyl palmitate, stearyl palmitate, cetyl stearate, isopropyl laurate, isopropyl myristate, isopropyl palmitate and the like and mixtures thereof; glycerol esters; ethers such as eucalyptol, cetearyl glucoside, dimethyl isosorbicide polyglyceryl-3 cetyl ether, polyglyceryl-3 decyltetradecanol, propylene glycol myristyl ether and the like and mixtures thereof; alkoxylated carboxylic acids; alkoxylated alcohols; fatty alcohols such as octyldodecanol, lauryl, myristyl, cetyl, stearyl and behenyl alcohol and the like and mixtures thereof; and the like and mixtures thereof. For example, a particularly well suited emollient is petrolatum. Other conventional emollients may also be added in a manner which maintains the desired properties of the lotion formulations set forth herein.

A wax in the lotion formulations may primarily function as an immobilizing agent for the emollient and any active ingredient. In addition to immobilizing the emollient and reducing it's tendency to migrate, the wax in the lotion formulation provides a tackiness to the lotion formulation which improves the transfer to the skin of the wearer. The presence of the wax also modifies the mode of transfer in that the lotion tends to fracture or flake off instead of actually rubbing off onto the skin of the wearer which can lead to improved transfer to the skin. The wax may further function as an emollient, occlusive agent, moisturizer, barrier enhancer and combinations thereof.

Suitable waxes which can be incorporated into the lotion formulation include animal, vegetable, mineral or silicone based waxes which may be natural or synthetic such as, for example, bayberry wax, beeswax, C30 alkyl dimethicone, candelilla wax, carnauba, ceresin, cetyl esters, esparto, hydrogenated cottonseed oil, hydrogenated jojoba oil, hydrogenated jojoba wax, hydrogenated microcrystalline wax, hydrogenated rice bran wax, japan wax, jojoba butter, jojoba esters, jojoba wax, lanolin wax, microcryustalline wax, mink wax, motan acid wax, motan wax, ouricury wax, ozokerite, paraffin, PEG-6 beeswax, PEG-8 beeswax, rezowax, rice bran wax, shellac wax, spent grain wax, spermaceti wax, steryl dimethicone, synthetic beeswax, synthetic candelilla wax, synthetic carnuba wax, synthetic japan wax, synthetic jojoba wax, synthetic wax, and the like and mixtures thereof. For example, a particularly well suited wax includes about 70 weight percent ceresin wax, about 10 weight percent microcrystalline wax, about 10 weight percent paraffin wax and about 10 weight percent cetyl esters (synthetic spermaceti wax).

To provide the improved transfer to the skin of the wearer, the lotion formulation may include from about 5 to about 95 weight percent, desirably from about 25 to about 75 weight percent, and more desirably from about 40 to about 60 weight percent of the wax. Lotion formulations which include an amount of wax less than the recited amounts tend to have lower viscosities which undesirable leads to migration of the lotion. Whereas, lotion formulations which include an amount of wax greater than the recited amounts tend to provide less transfer to the wearer's skin.

A viscosity enhancer may be added to the lotion formulation to increase the viscosity to help stabilize the formulation on the outwardly facing surfaces of the sheets 12 and 14, and thereby reduce migration and improve transfer to the skin. Desirably, the viscosity enhancer increases the viscosity of the lotion formulation by at least about 50 percent, more desirably at least about 100 percent, even more desirably by at least about 500 percent, yet even more desirably by at least about 1000 percent, and even more desirably by at least about 5000 percent. Suitable viscosity enhancers which can be incorporated into the lotion formulation include polyolefin resins, lipophilic/oil thickeners, ethylene/vinyl acetate copolymers, polyethylene, silica, talc, colloidal silicone dioxide, zinc stearate, cetyl hydroxy ethyl cellulose and other modified celluloses and the like and mixtures thereof. For example, a particularly well suited viscosity enhancer is an ethylene/vinyl acetate copolymer commercially available from E. I. Dupont De Ne Mours, a business having offices located in Wilmington, Del. under the trade designation ELVAX.

If it is desired that the lotion formulation treat the skin, it can also include an active ingredient such as a skin protectant. Skin protectants may be a drug product which protects injured or exposed skin or mucous membrane surface from harmful or irritating stimuli. Suitable active ingredients, in addition to those mentioned above as suitable emollients, which can be incorporated into the lotion formulation include, but are not limited to, alantoin and its derivatives, aluminum hydroxide gel, calamine, cocoa butter, dimethicone, cod liver oil, glycerin, kaolin and its derivatives, lanolin and its derivatives, mineral oil, shark liver oil, talc, topical starch, zinc acetate, zinc carbonate, and zinc oxide and the like, and mixtures thereof. The lotion formulation may include from about 0.10 to about 95 weight percent of the active ingredient depending upon the skin protectant and the amount desired to be transferred to the skin.

In order to better enhance the benefits to the wearer, additional ingredients can be included in the lotion formulations of the present invention. For example, the classes of ingredients that may be used and their corresponding benefits include, without limitation: antifoaming agents (reduce the tendency of foaming during processing); antimicrobial actives; antifungal actives; antiseptic actives; antioxidants (product integrity); astringents—cosmetic (induce a tightening or tingling sensation on skin); astringent—drug (a drug product which checks oozing, discharge, or bleeding when applied to skin or mucous membrane and works by coagulating protein); biological additives (enhance the performance or consumer appeal of the product); colorants (impart color to the product); deodorants (reduce or eliminate unpleasant odor and protect against the formation of malodor on body surfaces); other emollients (help to maintain the soft, smooth, and pliable appearance of the skin by their ability to remain on the skin surface or in the stratum corneum to act as lubricants, to reduce flaking, and to improve the skin's appearance); external analgesics (a topically applied drug that has a topical analgesic, anesthetic, or antipruritic effect by depressing cutaneous sensory receptors, of that has a topical counterirritant effect by stimulating cutaneous sensory receptors); film formers (to hold active ingredients on the skin by producing a continuous film on skin upon drying); fragrances (consumer appeal), silicones/organomodified silicones (protection, tissue water resistance, lubricity, tissue softness), oils (mineral, vegetable, and animal),; natural moisturizing agents (NMF) and other skin moisturizing ingredients known in the art; opacifiers (reduce the clarity or transparent appearance of the product); powders (enhance lubricity, oil adsorption, provide skin protection, astringency, opacity, etc.); skin conditioning agents; solvents (liquids employed to dissolve components found useful in the cosmetics or drugs); and surfactants (as cleansing agents, emulsifying agents, solubilizing agents, and suspending agents).

Referring to FIG. 8, the absorbent article 10 may also include a top sheet retainer flap 26 and a bottom sheet retainer flap 28. The construction and operation of these retainer flaps is discussed in detail in the published U.S. Pat. Application Ser. No. 2002/0058921 A1, incorporated herein by reference for all purposes. In general, the retainer flaps 26 and 28 may be strips of material having a generally constant width and attached at their edges to the outward faces of the top sheet 12 and back sheet 14 so that a cavity or space is defined between the flaps 26, 28 and their respective sheet 12, 14. The strips are desirably releasably adhered to their respective sheets so that the wearer can remove the strip from the sheet 12 or 14 that is intended to be the body-facing surface. For example, if the wearer intends for the top sheet 12 to be the body-facing surface of the article 10, she may remove the retainer flap 26 prior to placement of the article 10.

The retainer flaps 26 and 28 aid the wearer in placement of the article 10 by forming a cavity into which the wearer can insert her fingers and thereby retain the article 10 on her hand while she holds, handles and places the article 10 in the vestibule without touching the body-facing surface of the article 10. Similarly, for removing the used absorbent article 40 from the vestibule, the user can again insert her fingers into the cavity formed between the retainer flap 26 or 28 and adjacent sheet 12 or 14 and can thus readily retain the absorbent article 10 on her hand while she handles, moves, and removes, the absorbent article from her vestibule. The retainer flaps 26, 28 may be of a width so that after folding the article with the body-facing surfaces disposed inwardly, the retainer flap can be stretched, turned inside-out, and pulled over the open ends of the article without the wearer touching the body-facing surfaces of the article. The retainer flap thus also serves to provide the article with a convenient self contained disposal "bag." It may be desired that the retainer flaps 26, 28 are formed of an elastomeric stretchable material to aid in the stretching and folding process.

In an alternate embodiment as illustrated generally in FIG. 9, it may be desired to include a top sheet tab 30 and a back sheet tab 32 extending generally transversely from the top sheet 12 and back sheet 14, respectively. The purpose of these tabs 30, 32 is also to aid in placement and removal of the article 10. The tabs may be defined by pieces of material folded and adhered to their respective sheet. The tabs may be releasably adhered so that the wearer can remove the tab 30, 32 from the sheet 12,14 intended to be the body-facing surface of the article 10. The tabs provide a mechanism for a wearer to grasp the article 10 between here thumb and fingers of a hand to facilitate placement and removal of the article without touching the body-facing surface. The use of placement and removal tabs with interlabial absorbent articles is also described in the published U.S. Patent Application Ser. No. 2001/0025163 A1 incorporated herein by reference for all purposes.

It should be appreciated by those skilled in the art that various modifications and variations may be made to the embodiments of the invention illustrated or described herein without departing from the scope and spirit of the invention as set forth in the appended claims and their equivalents.

What is claimed is:

1. An interlabial absorbent article comprising:
a liquid permeable top sheet;
a polymeric film back sheet;
an absorbent material disposed between said top sheet and back sheet;
wherein said polymeric film back sheet is also liquid permeable such that said article may be disposed at generally any orientation within a wearer's vestibule and absorb bodily fluids at any such orientation; and
a first placement mechanism attached to said top sheet and a second placement mechanism attached to said back sheet, said placement mechanisms being removable such that a wearer may remove the placement mechanism from the respective said sheet intended to be the body-facing sheet prior to placement of said article.

2. The interlabial absorbent article as in claim 1, wherein said placement mechanisms comprise retainer flaps lying against said respective top sheet and back sheet.

3. The interlabial absorbent article as in claim 1, wherein said placement mechanism comprise tabs extending generally transversely from said respective top sheet and back sheet.

4. The interlabial absorbent article as in claim 1, wherein both of said top sheet and said polymeric film back sheet comprise a skin wellness additive that is coated on substantially the entire outwardly facing surfaces of said top sheet and said back sheet.

5. The interlabial absorbent article as in claim 4, wherein said skin wellness additive comprises a lotion formulation designed to address a skin health issue particular to the female vestibule.

6. The interlabial absorbent article as in claim 5, wherein said lotion formulation comprises any combination of an emollient, wax, and skin protectant agent.

7. The interlabial absorbent article as in claim 1, wherein said polymeric film back sheet is perforated to render it liquid permeable.

8. The interlabial absorbent article as in claim 1, wherein said polymeric film back sheet is embossed.

9. The interlabial absorbent article as in claim 1, wherein said top sheet is embossed.

10. The interlabial absorbent article as in claim 1, wherein said top sheet and said polymeric film back sheet are embossed.

11. The interlabial absorbent article as in claim 1, wherein said article is of a size so as to be folded along at least one fold line in use thereof.

12. The interlabial absorbent article as in claim 11, wherein said article is foldable along a plurality of fold lines.

13. The interlabial absorbent article as in claim 1, wherein said article has a symmetric shape with respect to a longitudinal axis thereof.

14. The interlabial absorbent article as in claim 1, wherein said article has a symmetric shape with respect to a transverse centerline axis thereof.

15. The interlabial absorbent article as in claim 1, wherein said article has one of a circular, oval, and rectangular shape.

* * * * *